(12) United States Patent
Demetriou et al.

(10) Patent No.: US 10,495,646 B2
(45) Date of Patent: Dec. 3, 2019

(54) N-ACETYL GLUCOSAMINE AS A BIOMARKER OF MS DISEASE COURSE

(71) Applicants: THE REGENTS OF THE UNIVERSITY OF CALIFORNIA, Oakland, CA (US); CHARITE-UNIVERSITATSMEDIZIN BERLIN, Berlin (DE); MT. SINAI HOSPITAL, Toronto (CA)

(72) Inventors: Michael Demetriou, Irvine, CA (US); Alexander Brandt, Berlin (DE); Friedmann Paul, Berlin (DE); James Dennis, Toronto (CA)

(73) Assignees: The Regents of the University of California, Oakland, CA (US); Charite-Universitatsmedizin Berlin, Berlin (DE); Mt. Sinai Hospital, Toronto (CA)

( * ) Notice: Subject to any disclaimer, the term of this patent is extended or adjusted under 35 U.S.C. 154(b) by 70 days.

(21) Appl. No.: 15/547,496

(22) PCT Filed: Jan. 29, 2016

(86) PCT No.: PCT/US2016/015807
§ 371 (c)(1),
(2) Date: Jul. 29, 2017

(87) PCT Pub. No.: WO2016/123565
PCT Pub. Date: Aug. 4, 2016

(65) Prior Publication Data
US 2018/0003717 A1 Jan. 4, 2018

Related U.S. Application Data

(60) Provisional application No. 62/109,831, filed on Jan. 30, 2015.

(51) Int. Cl.
*G01N 33/66* (2006.01)

(52) U.S. Cl.
CPC ......... *G01N 33/66* (2013.01); *G01N 2400/00* (2013.01); *G01N 2800/285* (2013.01); *G01N 2800/52* (2013.01)

(58) Field of Classification Search
CPC ......... G01N 2800/52; G01N 2800/285; G01N 33/66; G01N 2400/00
See application file for complete search history.

(56) References Cited

U.S. PATENT DOCUMENTS

| | | |
|---|---|---|
| 2004/0077023 A1 | 4/2004 | Dotan et al. |
| 2009/0099130 A1 | 4/2009 | Demetriou et al. |
| 2010/0209914 A1 | 8/2010 | Bigwood et al. |
| 2011/0085981 A1 | 4/2011 | Wang |
| 2012/0077686 A1 | 3/2012 | Weiner et al. |

FOREIGN PATENT DOCUMENTS

| | | |
|---|---|---|
| WO | 2006/117689 A2 | 11/2006 |
| WO | 2006/136841 A1 | 12/2006 |
| WO | 2013/162773 A1 | 10/2013 |

OTHER PUBLICATIONS

Grigorian, Ani et al., "N-Acetylglucosamine inhibits T-helper 1 (Th1)/T-helper 17 (Th17) cell responses and treats experimental autoimmune encephalomyelitis", The Journal of Biological Chemistry, Nov. 18, 2011. vol. 286, No. 46, pp. 40133-40141.

M. M. Verbeek et al: "Increased cerebrospinal fluid chitotriosidase index in patients with multiple sclerosis", Acta Neurologica Scandinavica., vol. 121, No. 5, May 1, 2010, pp. 309-314.

Vahid Shaygannejad et al: "Effects of adjunct glucosamine sulfate on relapsing-remitting multiple sclerosis progression: Preliminary findings of a randomized, placebo-controlled trial", Neurological Research, vol. 32, No. 9, Nov. 19, 2010, pp. 981-985.

*Primary Examiner* — Christopher Adam Hixson (57) ABSTRACT

The invention provides the art with a powerful diagnostic method of distinguishing relapse-remitting MS subjects from progressive MS subjects, based on the measurement of serum concentrations of N-acetylglucosamine (GlcNAc,), for the first time enabling rapid diagnosis of the progressive form of MS. GlcNAc serum concentration can also be used to assess neurodegenerative status and MS progression in subjects suffering from MS or other neurological conditions. The methods of the invention also allow for the identification of new therapeutics for MS and other neurological conditions and also enables the personalized efficacy assessment of a potential therapy for an MS subject.

4 Claims, 5 Drawing Sheets

N-ACETYL GLUCOSAMINE AS A BIOMARKER OF MS DISEASE COURSE

CROSS-REFERENCE TO RELATED APPLICATIONS

This application claims priority to International Application No. PCT/US2016/015807, entitled "N-Acetyl Glucosamine as a Biomarker of MS Disease Course," filed on Jan. 29, 2016, which claims priority to U.S. Provisional Application No. 62/109,831, entitled "N-Acetyl Glucosamine as a Biomarker of MS Disease Course," filed on Jan. 30, 2015, each of which is incorporated by reference herein in its entirety.

STATEMENT REGARDING FEDERALLY FUNDED RESEARCH OR DEVELOPMENT

Not Applicable.

BACKGROUND OF THE INVENTION

Multiple sclerosis (MS) is the most common chronic autoimmune disease of the central nervous system. The majority of patients diagnosed with MS have the relapsing-remitting form of the disease (RRMS). Relapses, defined as subacute aggravation of neurologic symptoms, determine clinical activity. Patients regularly remit days to weeks after relapse and either recover completely or are left with residual disability. After many years, some but not all patients convert to a progressive form where disability accumulates over time independent from relapses (secondary progressive MS). A few (10%-20%) patients show a progressive MS course from the beginning (primary progressive MS). The progressive MS course is primarily responsible for permanent neurological dysfunction. However, the factors determining the progressive disease course are unknown. Accordingly, clinically, no singular biomarkers exist to ascertain a disease course other than relapses and clinical progression themselves. Most importantly, and unlike RRMS, progressive MS lacks effective therapies causing great adversity for affected patients. A biomarker that could readily discriminate between the two forms would have great utility in speeding diagnosis, especially of the progressive form, potentially saving patients from ineffective and potentially harmful therapies.

One previous study, described in Dickens A M, Larkin J R, Griffin J L, et al. "A type 2 biomarker separates relapsing-remitting from secondary progressive multiple sclerosis," Neurology 2014; 83(17):1492-9, demonstrates that serum markers can be used to discriminate between the MS subtypes. However, this study relied on multiple metabolite profiles and computational models over full mass spectrometry spectra to achieve discrimination between RRMS and progressive MS. Single predictive biomarkers were not discovered.

In all metazoans, cell surface and secreted proteins are modified by post-translational addition of complex carbohydrates in the endoplasmic reticulum, forming glycoproteins in the N-glycosylation pathway. Branching complexity and number of N-glycans per protein molecule influence the concentration and endocytosis of surface glycoproteins. The synthesis rate of these complex carbohydrates is controlled by enzymatic activity in the endoplasmic reticulum and metabolic supply of substrates. The primary substrate of this pathway is N-acetylglucosamine (GlcNAc,), which is built into complex glycans by the Mgat enzyme family. Genetically induced alterations in Asn (N)-linked protein glycosylation has been shown to promote T cell mediated inflammatory demyelination as well as neurodegeneration. Oral supplementation of mice with GlcNAc has been shown to inhibit pro-inflammatory T cell responses in models of MS by enhancing N-glycan branching via increased substrate supply to Golgi glycosylation enzymes. Extracellular GlcNAc from dietary sources enters cells through macropinocytosis and is then salvaged into the hexosamine pathway for production of UDP-GlcNAc. It is further believed that ER-associated degradation may recycle GlcNAc within cells.

Despite the demonstrated physiological importance of GlcNAc, including its role in MS biology, it has not been previously established in the prior art whether GlcNAc is a natural constituent of human blood serum, and what association, if any, exists between GlcNAc serum levels and MS status or other measures of neurodegeneration.

SUMMARY OF THE INVENTION

Advantageously, the inventors of the present disclosure have demonstrated a strong relationship between serum GlcNAc concentrations and MS subtype. This discovery provides the art with a facile and accurate means to predict a patient's MS subtype by measurement of serum GlcNAc concentration. GlcNAc serum concentration also correlates well with various measure of neurodegenerative severity, including the clinical severity of MS in MS subjects, and may be used as an indicator of MS progression. Additionally, the discoveries disclosed herein provide the art with a facile means of screening for potential MS therapies and personalized assessment of MS therapy in individual patients.

BRIEF DESCRIPTION OF THE FIGURES

FIGS. 1A, 1B, 1C, and 1D.

FIGS. 3A, 3B, 3C, and 3D.

DETAILED DESCRIPTION OF THE INVENTION

Disclosed herein are novel relationships between serum GlcNAc concentrations and various MS and neurodegeneration parameters. The various embodiments of the invention are next described in detail.

Serum GlcNAc Measurement.

In one aspect, the invention is directed to the measurement of GlcNAc in human serum as a diagnostic tool. Measurement of GlcNAc in serum may be accomplished and means known in the art for the detetion of nanomolar levels of an analyte, including by liquid chromatography mass-spectroscopy methodologies as set forth in Example 1. In another embodiment, the invention encompasses the measurement of serum GlcNAc concentration in humans having a disease state to assess disease type or severity. The disease state may comprise any inflammatory, neurologic, or degenerative condition.

Serum GlcNAc and MS Subtype.

In one aspect, the invention is directed to a method of diagnosing MS subtype in subjects afflicted with MS by measurement of serum GlcNAc concentration. An MS subject, as used herein, means a human having MS symptoms or having been formally diagnosed with MS. While reference will be made to human subjects, it will be understood that the scope of the invention also extends to other animals, including test animals and animal models of MS and other neurodegenerative conditions.

The inventors of the present disclosure have advantageously discovered that MS subtype in MS subjects is highly correlated with GlcNAc serum concentration. MS subjects having a GlcNAc serum level slightly below that found in healthy controls are more likely to have the relapse-remitting form of MS. MS subjects having a GlcNAc serum concentration lower than that of the healthy control range and the relapsing-remitting range are more likely to have the progressive form of MS.

Healthy control subjects were found to have an average serum GlcNAc concentration of about 700 nM. No gender differences in serum GlcNAc concentration was observed. Serum GlcNAc concentrations increased with increasing age, by about 4.79 nM per year of age. In subjects previously diagnosed with relapse-remitting MS (RRMS), serum GlcNAc concentration was slightly reduced compared to healthy controls, averaging about 600 nM. In contrast, MS subjects previously diagnosed with progressive MS (PMS) had significantly reduced serum GlcNAc concentrations, in the range of 350-475 nM. No differences in serum GlcNAc concentration were observed between subjects having primary and secondary MS.

In one embodiment, the invention comprises a method of diagnosing an MS subject's MS subtype. In a first step, a serum sample is obtained from the MS subject. In a second step, the serum GlcNAc concentration is measured. In a third step, a diagnosis of MS subtype is made by comparing the subject's measured serum GlcNAc concentration with a progressive MS cutoff value, which has been selected to statistically distinguish subjects having progressive MS from subjects having RRMS. If the MS subject's serum GlcNAc concentration is above the selected progressive MS cutoff value, the subject is diagnosed as having the relapse-remitting form of MS. If the MS subject's serum GlcNAc is at or below the selected progressive MS cutoff value, the subject is diagnosed as having the progressive form of MS.

The progressive MS cutoff value is a statistical cutoff value which accurately discriminates some portion of RRMS subjects from PMS subjects. In one embodiment, the statistical cutoff value is determined by assessing serum GlcNAc values in plurality of RRMS and PMS subjects, for example subjects matched to the test subject by one or more factors such as race, ethnicity, nationality, diet, or other health factors. Any value which provides a statistically significant or clinically relevant discrimination between the two pools of MS subjects may be selected.

Cutoff values may be determined according to known statistical methods of binary classification, such as k-nearest neighbor algorithms, support vector machines, linear discriminant analysis, diagonal linear discriminant analysis, updown naive Bayesian algorithms, neural network algorithms, hidden Markov model algorithms, or any combination or variation thereof. Selected cutoff values can be based on desired confidence intervals, for example confidence intervals of at least about 50%; from about 50% to about 75%; from about 75% to about 80%; from about 80% to about 85%; from about 85% to about 90%; from about 90% to about 95%; or from 95% to about 100%.

In one embodiment, cutoff values may be selected by ROC curve analysis. As known in the art, ROC curves may be generated from measurements of serum GlcNAc concentration in pools of confirmed RRMS and PMS subjects, for example by plotting true positive rate vs. the false positive rate across a range of various serum GlcNA concentration cutoff values. The ROC curve may then be used to select a threshold cutoff value for discrimination of RRMS subjects from PS subjects. The threshold cutoff value can be selected based on criteria such as the acceptable levels of sensitivity and specificity. For example, if sensitivity and specificity are of equal importance, the cutoff serum GlcNAc concentration may be selected as the value which maximizes the sum of sensitivity and specificity. Alternatively, a cutoff value may be calculated as that which minimizes the Euclidean distance between the ROC curve and the point representing 100% true positive rate and 100% false positive rate. Alternatively, if specificity and sensitivity are of unequal importance, these values can be weighted in selection of the serum GlcNAc concentration cutoff value.

Exemplary ROC curve data is presented in Table 1. Table 1 includes a range of GlcNAc serum concentration cutoff values and the corresponding false positive rate and false negative rate observed at each cutoff value in a cohort of confirmed RRMS and PMS subjects. In one embodiment, the invention is a method of selecting a progressive MS threshold cutoff value comprising a first step of generating a ROC curve from the data in Table 1, and a second step of selecting a progressive MS cutoff value from the range of cutoff values used to generate the ROC curve.

In one embodiment, the selected progressive MS cutoff value is a serum GlcNAc concentration between 400 and 600 nM.

In one embodiment, the GlcNAc serum concentration of the subject being diagnosed is age-adjusted in order to account for the age effect on serum GlcNAc. For example, the age adjusted GlcNAc value may be normalized to an age of 40, referred to as the GlcNAc-40 value. The subject's GlcNAc-40 value may be calculated according to Equation 1:

$$\text{GlcNAc-40} = [\text{GlcNAc}_m] - (40 - A) * 4.7874 \qquad \text{Equation 1:}$$

wherein $\text{GlcNAc}_m$ is the measured GlcNAc serum value of the subject, and $A$ is the subject's age.

In one embodiment, the selected progressive MS cutoff value is a serum GlcNAc-40 concentration between 400 and 600 nM.

TABLE 1

Serum GlcNAc concentration cutoff values for discrimination of progressive subtype and corresponding False Positive Rate and True Positive Rate at that cutoff.

| GlcNAc Conc. Cutoff Value | False Positive Rate | False Negative Rate |
| --- | --- | --- |
| n/a | 100.0% | 0.0% |
| 1291.84 | 100.0% | 0.8% |
| 1282.85 | 100.0% | 1.6% |
| 1179.70 | 100.0% | 2.4% |
| 1075.03 | 100.0% | 3.2% |
| 1065.11 | 100.0% | 4.0% |
| 1053.59 | 100.0% | 4.8% |
| 1042.53 | 100.0% | 5.6% |
| 1033.94 | 100.0% | 6.4% |
| 1009.27 | 100.0% | 7.2% |
| 1001.56 | 100.0% | 8.0% |
| 996.58 | 100.0% | 8.8% |
| 977.96 | 100.0% | 9.6% |
| 976.79 | 98.2% | 9.6% |
| 956.91 | 98.2% | 10.4% |
| 952.96 | 98.2% | 11.2% |
| 947.41 | 98.2% | 12.0% |
| 942.66 | 98.2% | 12.8% |
| 941.49 | 98.2% | 13.6% |
| 939.75 | 98.2% | 14.4% |
| 939.58 | 98.2% | 15.2% |
| 923.77 | 98.2% | 16.0% |
| 921.56 | 98.2% | 16.8% |
| 899.77 | 98.2% | 17.6% |
| 898.71 | 98.2% | 18.4% |
| 895.44 | 98.2% | 19.2% |
| 887.16 | 98.2% | 20.0% |
| 879.35 | 98.2% | 20.8% |
| 873.83 | 98.2% | 21.6% |
| 872.67 | 98.2% | 22.4% |
| 849.71 | 98.2% | 23.2% |
| 842.66 | 98.2% | 24.0% |
| 842.23 | 98.2% | 24.8% |
| 839.07 | 96.4% | 24.8% |
| 838.97 | 96.4% | 25.6% |
| 837.27 | 96.4% | 26.4% |
| 832.35 | 96.4% | 27.2% |
| 832.17 | 96.4% | 28.0% |
| 811.62 | 96.4% | 28.8% |
| 794.02 | 96.4% | 29.6% |
| Serum Conc. Progressive MS Cutoff | | |
| 792.72 | 96.4% | 30.4% |
| 787.11 | 96.4% | 31.2% |
| 786.14 | 96.4% | 32.0% |
| 775.18 | 96.4% | 32.8% |
| 774.56 | 96.4% | 33.6% |
| 768.73 | 96.4% | 34.4% |
| 758.14 | 96.4% | 35.2% |
| 757.55 | 96.4% | 36.0% |
| 756.02 | 96.4% | 36.8% |
| 755.24 | 96.4% | 37.6% |
| 739.06 | 96.4% | 38.4% |
| 736.51 | 96.4% | 39.2% |
| 729.75 | 94.5% | 39.2% |
| 727.87 | 94.5% | 40.0% |
| 723.10 | 94.5% | 40.8% |
| 716.98 | 94.5% | 41.6% |
| 714.59 | 94.5% | 42.4% |
| 714.37 | 94.5% | 43.2% |
| 712.12 | 94.5% | 44.0% |
| 710.21 | 94.5% | 44.8% |
| 706.26 | 94.5% | 45.6% |
| 705.87 | 94.5% | 46.4% |
| 705.09 | 94.5% | 47.2% |
| 703.99 | 94.5% | 48.0% |
| 693.59 | 94.5% | 48.8% |
| 685.15 | 94.5% | 49.6% |
| 678.42 | 94.5% | 50.4% |
| 670.73 | 92.7% | 50.4% |
| 665.12 | 92.7% | 51.2% |
| 663.35 | 92.7% | 52.0% |
| 656.40 | 92.7% | 52.8% |
| 655.10 | 92.7% | 53.6% |
| 654.11 | 92.7% | 54.4% |
| 654.02 | 92.7% | 55.2% |
| 653.38 | 92.7% | 56.0% |
| 652.56 | 92.7% | 56.8% |
| 649.68 | 92.7% | 57.6% |
| 649.37 | 92.7% | 58.4% |
| 649.22 | 92.7% | 59.2% |
| 643.53 | 92.7% | 60.0% |
| Serum Conc. Cutoff Value | | |
| 642.83 | 92.7% | 60.8% |
| 637.79 | 92.7% | 61.6% |
| 629.99 | 92.7% | 62.4% |
| 628.79 | 92.7% | 63.2% |
| 621.79 | 92.7% | 64.0% |
| 621.56 | 92.7% | 64.8% |
| 621.42 | 92.7% | 65.6% |
| 619.90 | 92.7% | 66.4% |
| 613.41 | 92.7% | 67.2% |
| 612.39 | 92.7% | 68.0% |
| 611.25 | 92.7% | 68.8% |
| 607.24 | 92.7% | 69.6% |
| 604.74 | 92.7% | 70.4% |
| 603.72 | 92.7% | 71.2% |
| 602.44 | 90.9% | 71.2% |
| 601.24 | 90.9% | 72.0% |
| 600.63 | 90.9% | 72.8% |
| 600.40 | 90.9% | 73.6% |
| 597.65 | 90.9% | 74.4% |
| 586.55 | 90.9% | 75.2% |
| 584.59 | 90.9% | 76.0% |
| 570.39 | 90.9% | 76.8% |
| 564.92 | 90.9% | 77.6% |
| 564.40 | 90.9% | 78.4% |
| 563.17 | 90.9% | 79.2% |
| 562.57 | 89.1% | 79.2% |
| 557.26 | 89.1% | 80.0% |
| 548.32 | 89.1% | 80.8% |
| 547.33 | 89.1% | 81.6% |
| 535.74 | 87.3% | 81.6% |
| 534.27 | 87.3% | 82.4% |
| 530.62 | 87.3% | 83.2% |
| 523.74 | 85.5% | 83.2% |
| 514.51 | 85.5% | 84.0% |
| 512.33 | 85.5% | 84.8% |
| 505.34 | 85.5% | 85.6% |
| 488.52 | 85.5% | 86.4% |
| 487.68 | 85.5% | 87.2% |
| 487.13 | 85.5% | 88.0% |
| 481.64 | 85.5% | 88.8% |
| Serum Conc. Progressive MS Cutoff | | |
| 475.37 | 85.5% | 89.6% |
| 473.05 | 85.5% | 90.4% |
| 473.01 | 83.6% | 90.4% |
| 471.66 | 83.6% | 91.2% |

TABLE 1-continued

Serum GlcNAc concentration cutoff values for discrimination of progressive subtype and corresponding False Positive Rate and True Positive Rate at that cutoff.

| | False Positive Rate | False Negative Rate |
|---|---|---|
| 452.85 | 83.6% | 92.0% |
| 438.81 | 83.6% | 92.8% |
| 438.56 | 83.6% | 93.6% |
| 432.52 | 83.6% | 94.4% |
| 431.45 | 81.8% | 94.4% |
| 428.43 | 81.8% | 95.2% |
| 427.42 | 80.0% | 95.2% |
| 424.71 | 80.0% | 96.0% |
| 423.96 | 78.2% | 96.0% |
| 415.11 | 76.4% | 96.0% |
| 413.23 | 76.4% | 96.8% |
| 403.67 | 76.4% | 97.6% |
| 399.18 | 74.5% | 97.6% |
| 390.33 | 74.5% | 98.4% |
| 387.38 | 72.7% | 98.4% |
| 386.98 | 70.9% | 98.4% |
| 381.73 | 69.1% | 98.4% |
| 380.99 | 69.1% | 99.2% |
| 375.73 | 67.3% | 99.2% |
| 375.18 | 65.5% | 99.2% |
| 374.25 | 63.6% | 99.2% |
| 368.15 | 61.8% | 99.2% |
| 364.71 | 60.0% | 99.2% |
| 360.13 | 58.2% | 99.2% |
| 358.40 | 56.4% | 99.2% |
| 357.51 | 54.5% | 99.2% |
| 351.93 | 52.7% | 99.2% |
| 348.33 | 50.9% | 99.2% |
| 343.68 | 49.1% | 99.2% |
| 336.52 | 47.3% | 99.2% |
| 334.70 | 45.5% | 99.2% |
| 334.02 | 43.6% | 99.2% |
| 332.30 | 41.8% | 99.2% |
| 319.87 | 40.0% | 99.2% |
| 319.34 | 38.2% | 99.2% |
| 310.35 | 36.4% | 99.2% |
| Serum Conc. Progressive MS Cutoff | | |
| 310.28 | 34.5% | 99.2% |
| 300.28 | 32.7% | 99.2% |
| 297.32 | 30.9% | 99.2% |
| 293.90 | 29.1% | 99.2% |
| 291.63 | 29.1% | 100000.0% |
| 282.99 | 27.3% | 100000.0% |
| 264.94 | 25.5% | 100000.0% |
| 262.26 | 23.6% | 100000.0% |
| 248.76 | 21.8% | 100000.0% |
| 239.97 | 20.0% | 100000.0% |
| 239.09 | 18.2% | 100000.0% |
| 225.95 | 16.4% | 100000.0% |
| 213.66 | 14.5% | 100000.0% |
| 211.36 | 12.7% | 100000.0% |
| 195.89 | 10.9% | 100000.0% |
| 191.70 | 9.1% | 100000.0% |
| 169.14 | 7.3% | 100000.0% |
| 160.07 | 5.5% | 100000.0% |
| 149.02 | 3.6% | 100000.0% |
| 140.16 | 1.8% | 100000.0% |
| 98.98 | 0.0% | 100000.0% |

Monitoring.

Some portion of RRMS subjects will develop the progressive MS subtype. Because treatment regimens for RRMS and progressive MS are different, it would be beneficial to know when RRMS patients have developed progressive MS so that treatment can be adjusted accordingly. In one aspect, the invention encompasses regular monitoring of GlcNAc serum concentration in relapsing-remitting MS patients to to determine current disease subtype. In one embodiment, GlcNAc serum concentration measurements are made in an RRMS subject at regular time intervals or upon clinical events in order to determine if the subject has developed the progressive form. Upon such determination, treatment can be adjusted accordingly. Monitoring of disease status using GlcNAc can be performed at set time intervals (for example every six months or annually) or could be performed in response to relapse events or other clinical indicators of increased MS severity.

Neurodegeneration Assessed by GlcNAc Serum Concentration.

The inventors of the present disclosure have advantageously determined that lower serum GlcNAc concentrations are associated with more severe neurodegeneration and more severe MS progression. The effect was confirmed across a variety of measures of neurodegenerative severity, including measures of the degree of MS progression. Notably, the novel predictive tools disclosed herein are applicable beyond the context of MS. Because other neurodegenerative pathologies share common degenerative pathways, GlcNAc may be used to assess neurodegenerative status in subjects afflicted with other neurodegenerative conditions.

In one embodiment, the invention encompasses a method of assessing neurodegenerative status in a subject by measurement of serum GlcNAc concentration, wherein increased neurodegenerative severity is assessed as serum GlcNAc concentration decreases. The method comprises the steps of measuring serum GlcNAc concentration in a subject and determining the subject's neurodegenerative status as the predicted value of a neurodegenerative severity measure based upon an established mathematical relationship between serum GlcNAc concentration and the neurodegenerative severity measure. The mathematical relationship used to derive neurodegeneration status may be established in the general population, or in a pool of matched subjects, e.g. subjects matched to the test subject by factors such as age, race, disease status, and other health factors.

The measure of neurodegenerative severity may comprise any measure of neurological function, disease state, disease progression, or neurodegeneration. For MS subjects, the measure of neurodegenerative may comprise a measure of MS severity or progression. For example, in MS subjects, decreasing GlcNAc concentrations are found to correlate with reduced Expanded Disability Status Scale score (EDSS), increased Multiple Sclerosis Severity Score, reduced Multiple Sclerosis Functional Composite score (MSFC), increased global brain atrophy, increased grey matter atrophy, increased white matter atrophy, and increased retinal axonal degeneration.

Figure 3A:
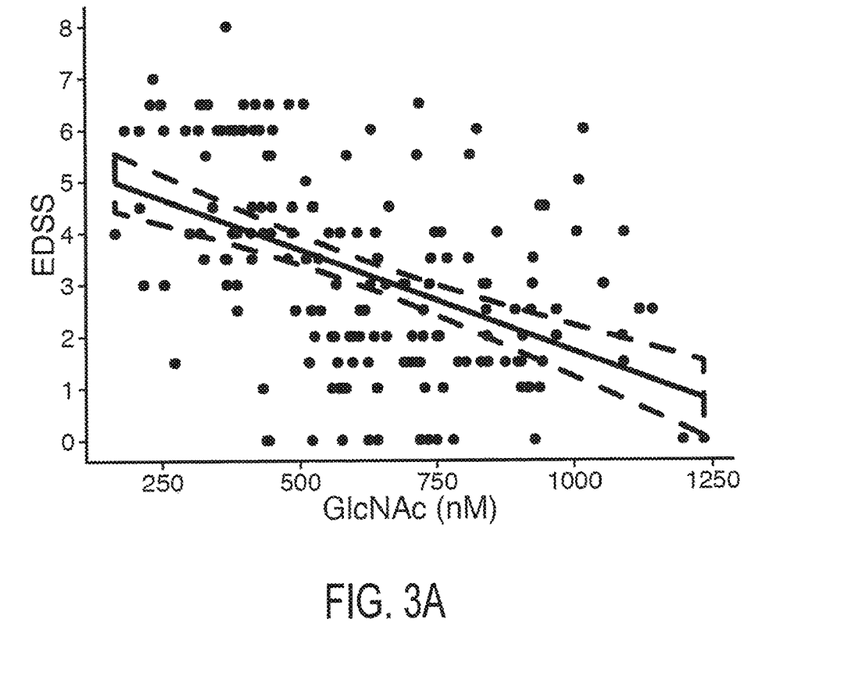
FIG. 3A depicts the relationship between serum GlcNAc concentration and Expanded Disability Status Scale score in MS subjects.

In one embodiment, the invention encompasses a method of predicting EDSS score based on a subject's serum GlcNAc concentration. In one embodiment, EDSS score is predicted using Equation 2:

$$\text{Predicted EDSS} = -0.0039208 * [\text{GlcNAc}_M] + 5.6300875 \quad \text{Equation 2:}$$

wherein EDSS is measured on a scale of 1 to 10 and $\text{GlcNAc}_M$ is measured GlcNAc serum concentration.

Figure 3B:
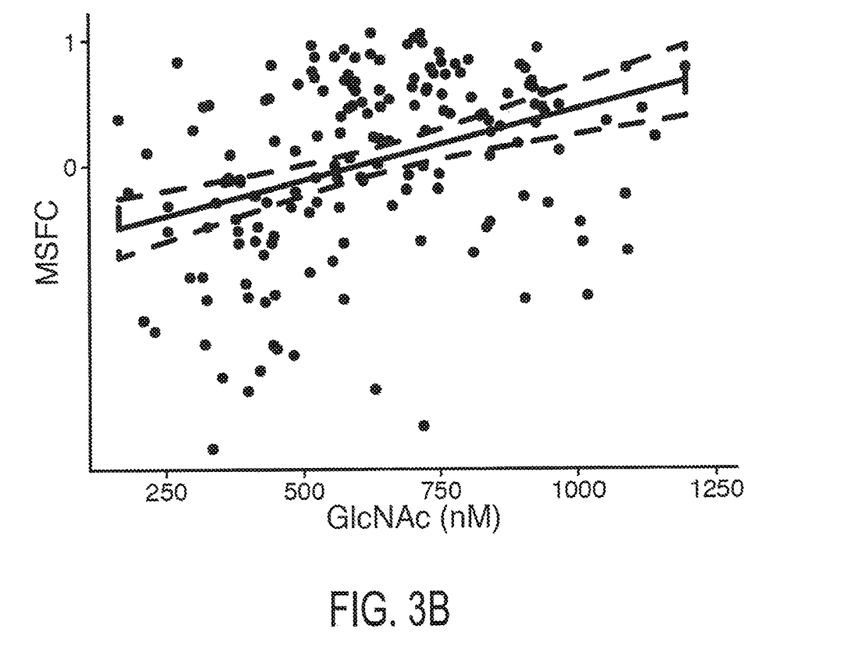
FIG. 3B depicts the relationship between serum GlcNAc concentration and Multiple Sclerosis Functional Composite score in MS subjects.
Figure 3C:
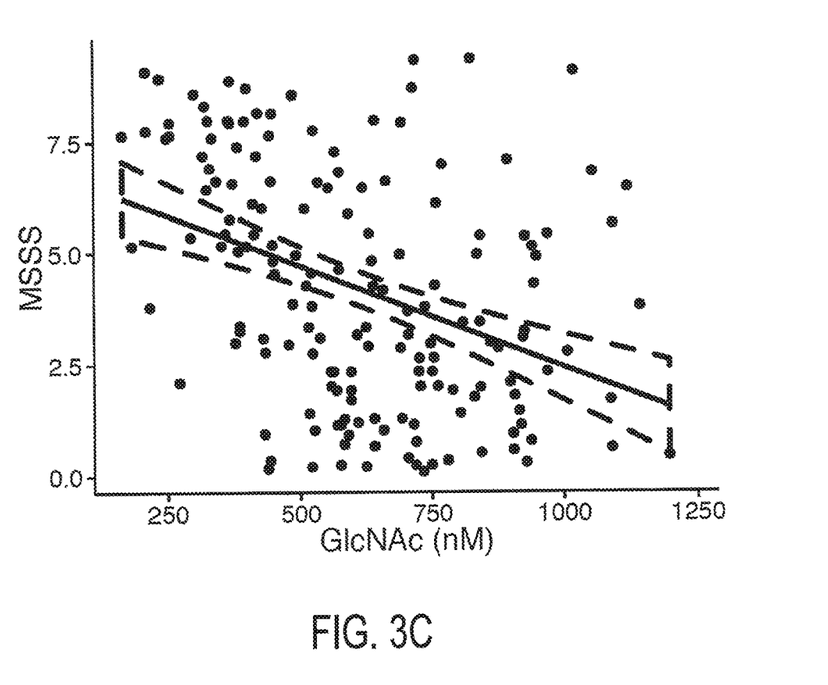
FIG. 3C depicts the relationship between serum GlcNAc concentration and Multiple Sclerosis Severity Score in MS subjects.

In one embodiment, the invention encompasses a method of predicting MSSS score based on a subject's serum GlcNAc concentration. In one embodiment, MSSS score is predicted using Equation 3:

$$\text{Predicted MSSS score} = -0.004538 * [\text{GlcNAc}_M] + 6.974223 \quad \text{Equation 3:}$$

wherein MSSS is the predicted MS Severity Score and $\text{GlcNAc}_M$ is measured GlcNAc serum concentration.

Figure 3D:
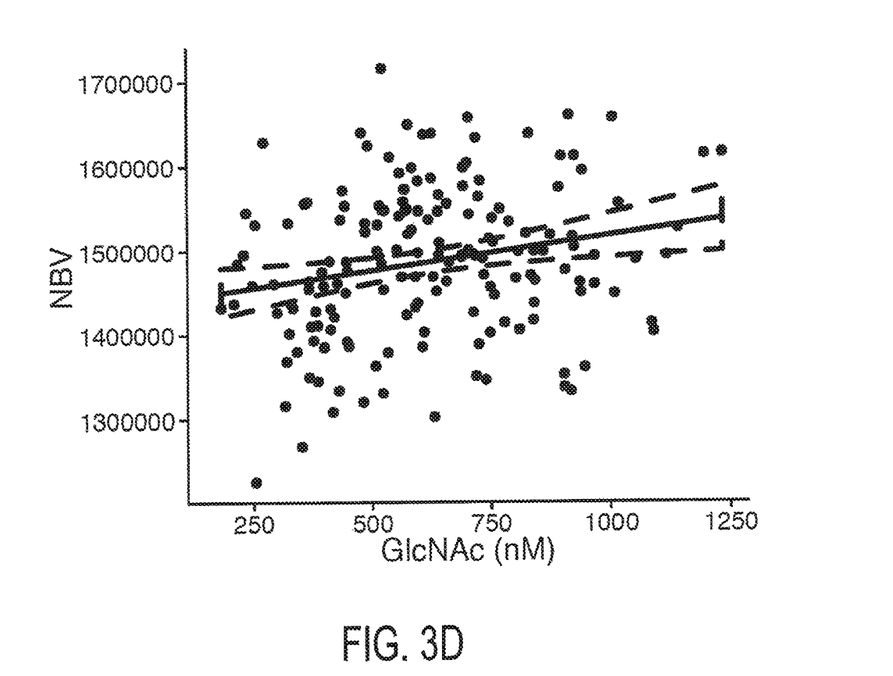
FIG. 3D depicts the relationship between serum GlcNAc concentration and normalized brain volume in MS subjects. The dotted lines represents a 95% confidence intervals.

In one embodiment, the invention encompasses a method of predicting normalized brain volume based on a subject's serum GlcNAc concentration. In one embodiment, normalized brain volume is predicted using Equation 4:

$$NBV = 83.69 * [GlcNAc_M] + 1,435,000 \quad \text{Equation 4:}$$

wherein NBV is predicted normalized brain volume in mm³, $GlcNAc_M$ is measured GlcNAc concentration is in nM. Brain atrophy may be assessed by comparing the predicted normalized brain volume in the subject with a standard value (e.g. average healthy brain volume) or a predicted normalized brain value previously attained for the subject, wherein a reduced normalized brain volume compared to the control standard indicates brain atrophy.

In one embodiment, the invention encompasses a method of predicting normalized grey matter volume based on a subject's serum GlcNAc concentration. In one embodiment, normalized gray matter brain volume is predicted using Equation 5:

$$NGMV = 48.86 * [GlcNAc_M] + 719,122 \quad \text{Equation 5:}$$

wherein NGMV is predicted normalized grey matter volume in mm³ and $GlcNAc_M$ is measured GlcNAc concentration in nM.

In one embodiment, the invention encompasses a method of predicting normalized white matter volume based on a subject's serum GlcNAc concentration. In one embodiment, normalized gray matter brain volume is predicted using Equation 6:

$$NWMV = 34.83 * [GlcNAc_M] + 715,599 \quad \text{Equation 6:}$$

wherein NGMV is predicted normalized grey matter volume in mm³ and $GlcNAc_M$ is measured GlcNAc concentration in nM.

In one embodiment, the invention encompasses a method of predicting retinal nerve fiber layer thickness based on a subject's serum GlcNAc concentration. In one embodiment, retinal nerve fiber layer thickness score is predicted using Equation 7:

$$\text{Predicted RNFL} = 0.01245 * [GlcNAc_M] + 85.01336 \quad \text{Equation 7:}$$

wherein RNFL is predicted retinal nerve fiber layer measured in microns, and $GlcNAc_M$ is measured GlcNAc concentration. Retinal axon degeneration in the subject can be assessed from RNFL by comparing the predicted value to a standard value (e.g. the average thickness in healthy subjects) or to a predicted RNFL value attained previously from the subject, wherein a reduced RNFL thickness relative to the selected comparison value indicates retinal axon degeneration.

N-glycan branching in T-Cells has been shown in animal models to regulate pro-inflammatory T-cell responses. The inventors of the present disclosure have advantageously determined that N-glycan branching in human T-cells correlates positively with GlcNAc serum levels. Accordingly, the measurement of GlcNAc serum levels in humans provides a means to assess inflammatory processes and other pathways which respond to GlcNAc serum levels.

Screening and Personalized Medicine Methods.

In another aspect, the scope of the invention encompasses screening methods of identifying therapeutic agents for the amelioration of MS severity and for the treatment of other neurodegenerative conditions. For example, in one embodiment, the invention comprises a method of discovering or validating putative treatments which: increase serum GlcNAc concentration; reverse or slow neurodegenerative processes; ameliorate the symptoms of MS; or which slow the progression of MS. In one embodiment, the test subject for the method is a human subject having MS or another neurodegenerative condition, a test animal, or an animal model of MS or another neurodegenerative condition. It will be understood that in vitro assays, e.g. performed on a tissue explant, or cultured cells, are also within the scope of the invention. The putative treatment may comprise administration of a therapeutic small molecule or biological species (e.g. peptide, antibody, etc.), a diet supplement, or any other treatment modality. The method comprises the steps of applying the treatment to one or more subjects, and measuring the effect of the treatment on serum GlcNAc concentration in the one or more subjects, for example by comparison to untreated controls or pre-treatment serum GlcNAc concentrations. If the putative treatment is observed to cause an increase in serum, tissue, or cellular GlcNAc concentrations in the one or more subjects, the treatment is deemed effective.

In another embodiment, in the context of personalized medicine for example, the invention comprises assessment of an individual patient's responsiveness to a treatment. For example, an MS subject or a subject having another neurodegenerative condition may be treated with a putative treatment, and if the subject's serum GlcNAc concentration increases, the treatment is deemed effective for that subject.

In another embodiment, the invention encompasses a method of identifying a predictive biomarker of MS severity or neurodegenerative severity, comprising the steps of measuring both the abundance of a putative predictive biomarker and the serum GlcNAc serum concentration in a plurality of subjects, wherein the biomarker is deemed predictive of neurodegenerative severity, or MS severity/progression if its abundance changes in a predictable manner with varying GlcNAc serum concentration.

In another embodiment, the invention encompasses a method of identifying a predictive biomarker of progressive MS status, comprising the steps of measuring both the abundance of a putative predictive biomarker and the serum GlcNAc serum concentration in a plurality of MS subjects, wherein the biomarker is deemed predictive of progressive MS status if its abundance changes in a predictable manner with varying GlcNAc serum concentration.

Example 1. GlcNAc Measurement and Discrimination of MS Subtype

Patients and healthy controls from the initial cohort were recruited at the neuroimmunology outpatient clinic at University of California Irvine, Calif. Patients from the confirmatory cohort were recruited at the NeuroCure Clinical Research Center, Berlin, Germany. Inclusion criteria in both cohorts were relapsing-remitting or progressive MS based on the 2010 revised McDonald criteria with disease course determined according to the 1996 Lublin criteria, stable immunomodulatory therapy with glatiramer acetate (relapsing-remitting) or no treatment (progressive), and age between 18 and 65. Exclusion criteria were acute relapse within the 6 months prior to inclusion.

Patients in the interventional cohort were recruited at the neuroimmunology outpatient clinic at University of California Irvine, Calif.

Clinical Scoring.

Patients' clinical examination was performed according to Kurtzke's Expanded Disability Status Scale (EDSS). Additionally, patients' clinical disability was assessed using the Multiple Sclerosis Functional Composite (MSFC), comprising the Timed 25-ft walk test (T25FW), the 9-hole peg test (9-HPT) and the 3 second Paced Auditory Serial Additions Test (PASAT). T25FW was performed twice and the 9-HPT twice for the dominant and non-dominant hands. The total MSFC z-score was calculated according to the official MSFC Administration and Scoring manual. Multiple Sclerosis Severity Scores (MSSS) were calculated from time since onset and EDSS using conversion factors known in the art.

Targeted LC-MS/MS.

Serum samples for metabolomics analysis were prepared as described as in Abdel Rahman A M, Ryczko M, Pawling J, Dennis J W. Probing the hexosamine biosynthetic pathway in human tumor cells by multitargeted tandem mass spectrometry. ACS Chem Biol 2013; 8(9):2053-62. Briefly, 50 µL serum (stored at −80° C.) and 200 µl ice cold extraction solvent (40% acetonitrile: 40% methanol: 20% $H_2O$), were vortexed for 2 minutes, then shaken at 1400 rpm, 4° C. for 1 hour and centrifuged at 4° C. for 10 minutes at ~18,000×g in a microfuge. Supernatants were transferred to a clean tube and evaporated in in a vacuum concentrator. Dried samples were stored at −80° C. Sample was resuspended in 100 µl of water containing the Internal Standards $D^7$-Glucose at 0.2 mg/mL and $D^9$-Tyrosine at 0.02 mg/ml. Samples were resolved by LC-MS/MS, in negative mode at the optimum polarity in MRM mode on an electrospray ionization (ESI) triple-quadrupole mass spectrometer. MULTIQUANT™ software (AB Sciex, Version 2.1) was used for peak analysis and manual peak confirmation. The results, expressed as area ratio (area of analyte/area of internal standard), were exported to a spreadsheet and analyzed with METABO-ANALYST™ 3.0. Standard curves were prepared by adding increasing concentrations of GlcNAc or N-Acetyl-D-[UL-$^{13}C_6$]glucosamine ([UL$^{13}C_6$] GlcNAc) to 50 µl aliquot of control serum. This allowed calculation of a calibration curve for GlcNAc serum levels, obtaining absolute values rather than relative concentrations. Analysts were blinded in regard to sample origin (HC or MS patients).

Glycosylation in T-Cells.

To establish if GlcNAc serum levels are linked to T-cell receptor glycosylation peripheral blood monocytic cells (PBMCs) stained with leukoagglutinin (L-PHA) were cultured before and after GlcNAc was added. L-PHA is a tetravalent plant lectin and binds specifically to glycans with GlcNAc branches.

Magnetic Resonance Imaging.

MRI was performed at 1.5 Tesla using three-dimensional T1-weighted magnetization prepared rapid acquisition and multiple gradient echo sequences (MPRAGE). Images were either acquired on a SONATA™ MRI (Siemens Medical Systems, Erlangen, Germany) with TE 4.38 ms, TR 2,110 ms, TI 1.1 ms or on an AVANTO™ MRI (Siemens Medical Systems, Erlangen, Germany) with TE 3.09 ms, TR 1,900 ms, TI 1.1 ms both with flip angle 15° and resolution 1 mm³. Brain atrophy was determined using MPRAGE scans with the FSL 5.0 (FMRIB Software Library, Oxford, UK) pipeline SIENAX. As pre-processing steps prior to SIENAX each scan was cropped to a field of view resembling the MNI standard space template shipped with FSL and subsequently corrected for non-uniformity using the N3 algorithm as implemented in the MIPAV package version 5.4.2.SIENAX then computed global brain volume estimates (NBV) as well as grey matter (NGMV) and white matter (NWMV) volume estimates normalized with respect to the individual's head size for accounting for inter-individual variability.

Optical Coherence Tomography.

Retinal nerve fiber layer thickness (RNFL) from both eyes was measured with a STATUS OCT™, software version 4.0 (Carl Zeiss Meditec, Dublin, Calif.) using the fast RNFL 3.4 protocol as previously described in Don J, Wernecke K D, Bock M, et al. Association of Retinal and Macular Damage with Brain Atrophy in Multiple Sclerosis. PLoS ONE 2011; 6(4):e18132. Briefly, patients were examined without pupil dilation. Only images with acceptable quality were included in the analysis, defined as visually even signal distribution, a reflectance signal strong enough to identify the RNFL layer borders, and a signal strength of ≥8 of 10. RNFL segmentation was manually corrected in case of segmentation errors.

Statistical Analysis.

Statistical analyses were performed with R PROJECT™ version 3.2.2 using RSTUDIO™ version 0.99.489 (RStudio, Boston, Mass., USA). Correlation between age or sex and GlcNAc serum levels were analyzed with linear regression models for age and Welch's t-test for sex in healthy controls. Correlations of GlcNAc serum levels with L-PHA staining on different cell populations were analyzed with linear regression models. Group differences between HC, RRMS and progressive MS patients were analyzed using analysis of variance (ANOVA). Receiver Operating Characteristics curves were calculated with R package ROCR 1.0-7. Correlation between GlcNAc serum level and clinical scores as well as imaging parameters was analyzed with linear regression models with GlcNAc serum level as independent variable. RNFL differences were analyzed with using generalized estimating equating models (GEE) using working correlation matrix "Exchangeable" to account for inter-eye within-patient effects and using GlcNAc serum level as independent variable. GlcNAc serum levels before and during oral treatment with GlcNAc were compared using one-sided paired t-tests, comparing the averaged weekly measurements in the four weeks before treatment with the averaged weekly measurements in the weeks during treatment in each patient. Significance in all tests was established at $p<0.05$.

Serum GlcNAc in Healthy Controls.

Figure 2:
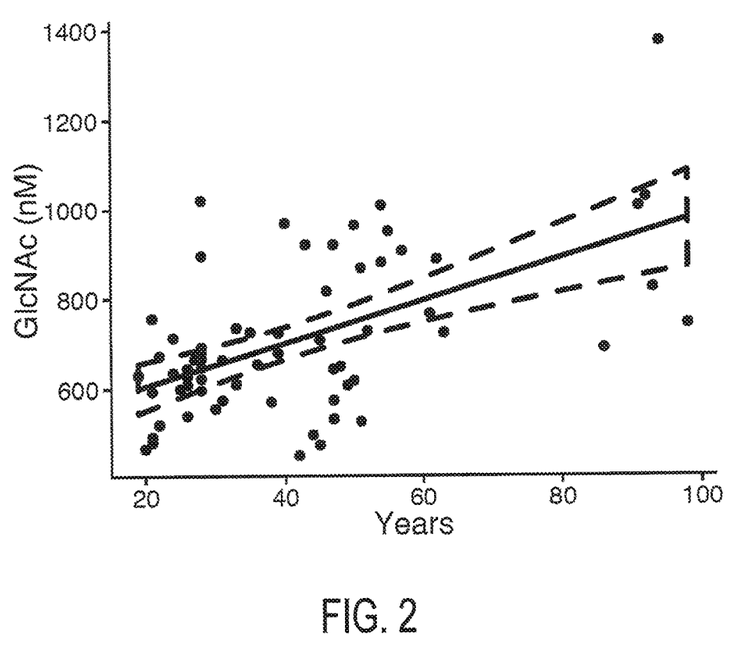
FIG. 2 is a plot depicting the effect of age on serum GlcNAc concentration. The dotted line represents a 95% confidence interval.

In healthy humans (n=66, 38 female/28 male, age 42.0±20.0 years) GlcNAc serum concentration was found to be 710.1±173.7 nM (range 452.0-1374.2 nM). GlcNAc concentration increased with age (Beta=4.787, SE=0.905, $r^2$=0.30, $p<0.0001$, meaning GlcNAc serum concentration increased by 4.79 nM per year of age, assumung a linear relationship as suggested by the data. There was no difference in GlcNAc serum concentration between male and female healthy subjects (male: 589.6±247.8 nM, female: 634.5±218.4 nM, F=0.0, p=0.988; and also no significant age-difference between male and female subjects (t=1.449, p=0.15). T-cell glycosylation was associated with GlcNAc serum levels ($r^2$=0.09, p=0.0206, n=59.

Figure 1A:
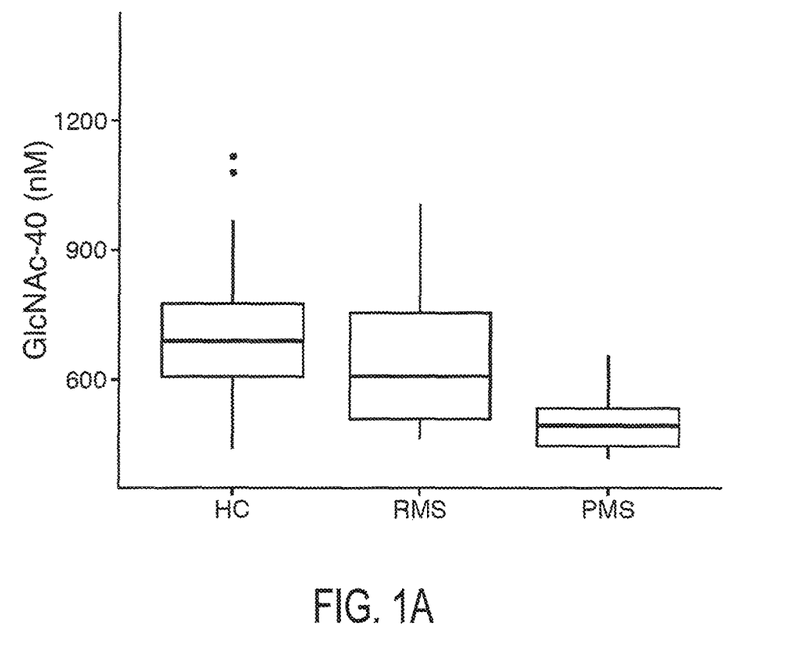
FIG. 1A depicts mean serum GlcNAc concentrations in a first cohort of subjects, including healthy controls (HC), relapsing-remitting MS subjects (RMS) and progressive subtype MS subjects (PMS).
Figure 1B:
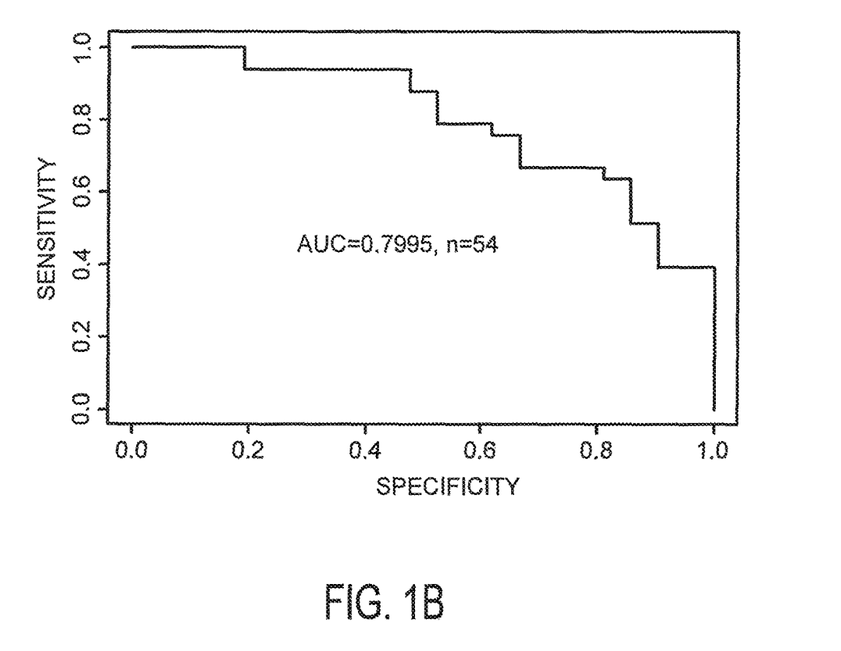
FIG. 1B depicts an ROC curve generated from the data summarized in 1A.

GlcNAc Serum Concentration. Sera from 33 MS patients was analyzed with relapsing-remitting and 21 sera from patients with progressive MS ("Initial Cohort"). To reflect increasing GlcNAc serum levels with age-adjusted GlcNAc serum levels were calculated by normalizing to an age of 40 years ("GlcNAc-40"). Healthy control age-adjusted GlcNAc-40 in the above cohort was 700.7±144.9 nM (range 442.4-1115.6 nM). Patients with relapsing disease course had slightly reduced age-adjusted GlcNAc-40 serum levels (632.8±162.4 nM, range 399.2-1006.5 nM, F=4.45, p=0.037). Progressive MS patients had severely reduced GlcNAc serum levels (475.3±90.5 nM, range 307.2-656.2 nM) both compared to HC (F=45.0, $p<0.0001$) and relapsing MS patients (F=16.4, p=0.0002). There was no GlcNAc-40 difference between primary (484.1±44.9 nM, n=2) and secondary progressive (474.3±95.4 nM, n=19) MS patients (F=0.02, p=0.89). In a ROC curve analysis, GlcNAc serum levels were able to discriminate excellently between relapsing-remitting and progressive MS patients with AUC=0.7995 (GlcNAc-40) and AUC=0.7359 (GlcNAc).

Confirmatory Analysis.

Figure 1C:
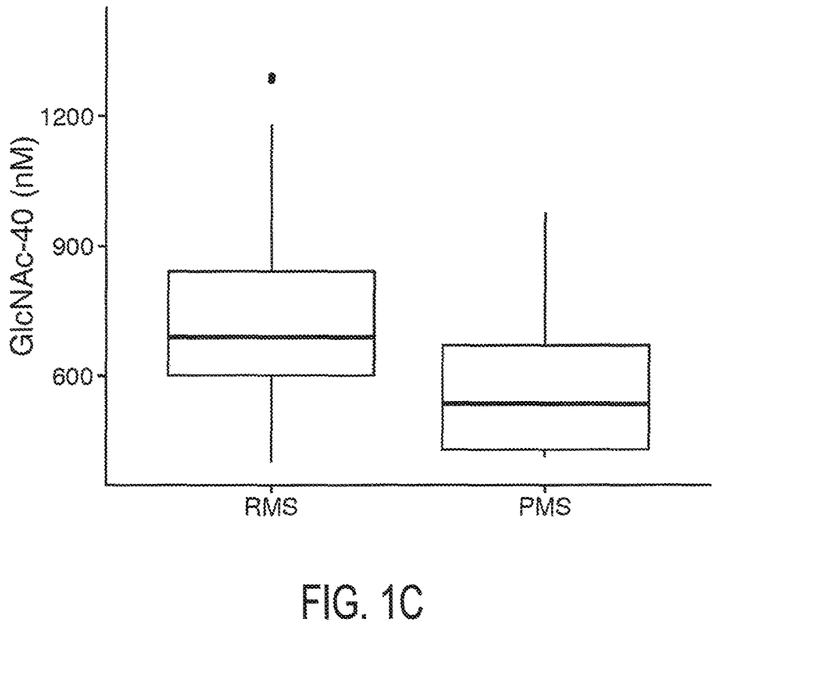
FIG. 1C depicts mean serum GlcNAc concentrations in a second cohort of MS subjects including relapsing-remitting MS subjects (RMS) and progressive subtype MS subjects (PMS).
Figure 1D:
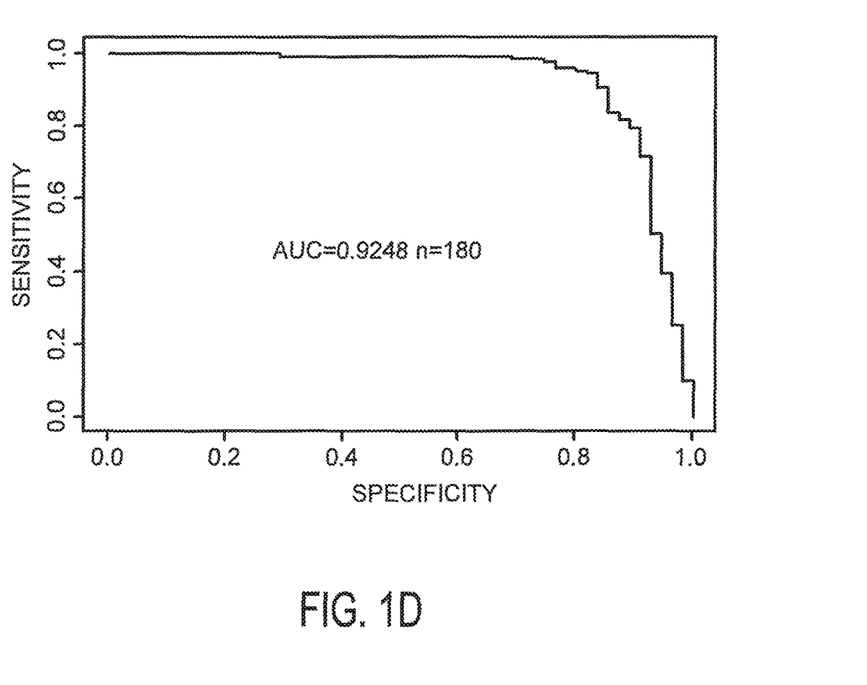
FIG. 1D depicts an ROC curve generated from the data summarized in 1C.

To confirm these findings, a second, independent cohort of 180 MS patients ("Confirmatory cohort") was studied. In this cohort, clinical disability and imaging parameters for neurodegeneration were collected, allowing investigation of the association of serum GlcNAc concentration with disease severity measures. Age-adjusted GlcNAc-40 serum levels were severely reduced in progressive MS ($362.3\pm165.4$ nM) in comparison to relapsing-remitting MS ($709.3\pm271.8$ nM, F=134, p<0.0001). Likewise, GlcNAc-40 levels were able to excellently discriminate between relapsing and progressive MS patients (ROC, AUC=0.9248; AUC=0.9047 when using unadjusted GlcNAc serum levels). Again, GlcNAc-40 levels between primary ($397.1\pm225.6$ nM, n=23) and secondary progressive ($337.3\pm99.9$ nM, n=32) MS patients were similar (F=1.78, p=0.19).

GlcNAc Serum Level Association with Clinical Disability and Neurodegeneration.

To investigate the association of GlcNAc serum levels with clinical disability, common measures for clinical severity in MS were assessed. In all cases, lower GlcNAc serum levels were associated with worse clinical disability: Lower GlcNAc serum level correlated well with worse EDSS (Beta=−0.0039, SE=0.0006, $r^2$=0.22, p<0.0001) and worse MSFC (Beta=0.0011, SE=0.0002, $r^2$=0.12, p<0.0001). There was no significant correlation between lower GlcNAc serum levels and longer time since diagnosis (Beta=−0.046, SE=0.029, p=0.1151); but with worse MSSS, a parameter calculated from the current EDSS and disease duration of a patient as a measurement for disease severity (Beta=−0.0045, SE=0.0008, $r^2$=0.15, p<0.0001).

Several imaging parameters reflecting chronic neurodegeneration and disease progression in MS were analyzed. Lower GlcNAc serum levels were associated with more severe global brain atrophy (NBV, Beta=83.7, SE=30.0, $r^2$=0.05, p=0.0058), grey matter atrophy (NGMV, Beta=48.9, SE=19.0, $r^2$=0.04, p=0.0112) and white matter atrophy (NWMV, Beta=34.8, SE=15.0, $r^2$=0.03, p=0.0213) Likewise, lower GlcNAc serum levels were associated with more severe retinal axonal degeneration measured with OCT (RNFL, B=0.0124, SE=0.0034, p=0.0004).

Oral GlcNAc Supplementation.

P progressive MS patients (n=13, age $52.9\pm13.6$ years, sex 4M/9F) were treated over four weeks with 3 g oral GlcNAc per day. T-cell L-PHA staining as a correlate of N-glycosylation increased from an average $98.7\pm5.3\%$ in the four weeks before treatment to an average $103.3\pm7.4\%$ in the four weeks during treatment (T=3.23, p=0.0036), showing a causal relationship between GlcNAc serum levels and T-cell receptor glycosylation in humans.

Conclusions.

The results show that GlcNAc is endogenous to human serum and regulates N-glycan branching in human T cells in vivo. Aging in humans is associated with increases in serum GlcNAc levels. Analysis of two independent MS cohorts reveals that serum GlcNAc is markedly reduced in progressive MS, and correlates inversely with clinical disability and neurodegeneration in brain and retina.

The study establishes serum GlcNAc concentration as a physiological biomarker to discriminate relapsing and progressive MS. The consistent correlation of GlcNAc serum levels to clinical disease severity and brain atrophy emphasizes the role of N-glycosylation in the pathophysiology of MS. It is further conspicuous that primary and secondary progressive MS patients did not differ in serum GlcNAc levels, making an early involvement of N-glycosylation in MS pathophysiology likely.

All patents, patent applications, and publications cited in this specification are herein incorporated by reference in their entirety to the same extent as if each independent patent, patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of treating an MS patient, wherein the patient is receiving an ongoing treatment for the relapse-remitting form of MS, comprising the steps of
   measuring the serum GlcNAc concentration of the subject; and
   determining if the patient has the progressive form of MS by assessing whether the measured GlcNAc serum concentration is below a selected progressive MS serum GlcNAc concentration cutoff value, and
   continuing the treatment for the relapse-remitting form of MS if it is determined that the patient does not have the progressive form of MS, or
   halting the treatment for the relapse-remitting form of MS if it is determined that the patient has the progressive form of MS.

2. The method of claim 1, wherein
   the progressive MS serum GlcNAc concentration cutoff value is a value between 400 and 600 nM.

3. The method of claim 1, wherein
   the subject's measured serum GlcNAc concentration is normalized to a selected age and is compared against a progressive MS threshold normalized to the selected age.

4. The method of claim 1, wherein
   the assessment of serum GlcNAc concentration is made following a relapse event or the manifestation of a clinical indicator of increased MS severity.

* * * * *